US00PP26194P3

(12) United States Plant Patent
Ackerman et al.

(10) Patent No.: US PP26,194 P3
(45) Date of Patent: Dec. 8, 2015

(54) STRAWBERRY PLANT NAMED 'PE-3.222'

(50) Latin Name: *Fragaria ananassa*
Varietal Denomination: PE-3.222

(71) Applicant: PLANT SCIENCES, INC., Watsonville, CA (US)

(72) Inventors: Stephen M. Ackerman, Salinas, CA (US); Steven D. Nelson, Watsonville, CA (US); Michael D. Nelson, Watsonville, CA (US)

(73) Assignee: Plant Sciences, Inc., Watsonville, CA (US)

( * ) Notice: Subject to any disclaimer, the term of this patent is extended or adjusted under 35 U.S.C. 154(b) by 110 days.

(21) Appl. No.: 13/999,048

(22) Filed: Jan. 8, 2014

(65) Prior Publication Data

US 2015/0195978 P1 Jul. 9, 2015

(51) Int. Cl.
*A01H 5/00* (2006.01)

(52) U.S. Cl.
USPC ..... Plt./209

(58) Field of Classification Search
USPC ..... Plt./209
See application file for complete search history.

*Primary Examiner* — Annette Para
(74) *Attorney, Agent, or Firm* — Foley & Lardner LLP

(57) ABSTRACT

This invention relates to a new and distinct variety of strawberry plant named 'PE-3.222'. This new strawberry plant named 'PE-3.222' is primarily adapted to the growing conditions of the central coast of California, and is primarily characterized by its orange red to red fruit color, large, conical fruit with medium to strong gloss and very good flavor, medium to small plant size, small, medium green foliage that is slightly flat to concave in cross section, and short fruiting trusses that are short and held beneath the plant.

4 Drawing Sheets

Latin name of the genus and species of the plant claimed: *Fragaria ananassa.*

Variety denomination: 'PE-3.222'.

BACKGROUND OF THE INVENTION

The present invention relates to a new and distinct strawberry variety named 'PE-3.222'. This new variety is a result of a controlled cross made in 2003 in an ongoing breeding program between strawberry selection designated 'PS-3003' (unpatented) and strawberry variety designated 'PS-4634' (U.S. Plant Pat. No. 17,487). Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Ventura County, Calif. in the fall of 2005. After its selection, the new variety was asexually propagated by stolons in both San Joaquin County, Calif. and Siskiyou County, Calif. The new variety was extensively tested over the next several years in fruiting fields in Ventura County, Calif. This propagation has demonstrated that the combination of traits disclosed herein as characterizing the new variety are fixed and remain true to type through successive generations of asexual reproduction.

BRIEF SUMMARY OF THE INVENTION

'PE-3.222' is primarily adapted to the climate and growing conditions of the central coast of California. The nearby Pacific Ocean provides the needed humidity and moderate temperatures to produce a strong vigorous plant and maintain fruit quality during the fall production months.

The following traits have been repeatedly observed and are determined to be unique characteristics of 'PE-3.222', which in combination distinguish this strawberry plant as a new and distinct variety:

1. Orange red to red fruit color;
2. Large, conical fruit with medium to strong gloss and very good flavor;
3. Medium to small plant size;
4. Small, medium green foliage that is slightly flat to concave in cross section; and
5. Fruiting trusses that are short and held beneath the plant.

The strawberry variety that is believed to be most closely related to the new variety 'PE-3.222' is 'VALOR' (U.S. Plant Pat. No. 20,394). In side-by-side comparisons to the similar strawberry variety 'VALOR', 'PE-3.222' differs by the following combination of characteristics as described in Table 1.

TABLE 1

COMPARISON WITH THE STANDARD VARIETY

| Characteristic | 'PE-3.222' | 'VALOR' (US PP20,394) |
|---|---|---|
| Fruit color -- | Ranges from orange to orange red. | Ranges from red to dark red. |
| Fruit size -- | Large. | Medium. |
| Fruit gloss -- | Ranges from medium to strong. | Medium. |
| Fruit flavor -- | Very good | Good. |
| Plant size -- | Ranges from medium to small. | Medium. |
| Foliage size -- | Small. | Medium. |

For identification, a series of molecular markers have been determined for this new variety.

'PE-3.222' differs from its parents, 'PS-3003' and 'PS-4634', by the following combination of characteristics as described in Table 2.

TABLE 2

COMPARISON WITH THE PARENT VARIETIES

| Characteristic | 'PE-3.222' | 'PS-3003' | 'PS-4634' |
|---|---|---|---|
| Type of bearing -- | Everbearing. | Everbearing. | Summer bearing. |
| Plant size -- | Medium. | Medium. | Large. |
| Fruit color-- | Ranges from orange to orange red. | Orange red. | Ranges from orange red to red. |
| Fruit size -- | Large. | Small. | Very large. |

BRIEF DESCRIPTIONS OF THE PHOTOGRAPHS

The accompanying color photographs illustrate the overall appearance of typical specimens of the new strawberry variety 'PE-3.222', at various stages of development as true as it is reasonably possible with color reproductions of this type. Color in the photographs may differ slightly from the color value cited in the botanical descriptions which accurately describe the color of 'PE-3.222'. The depicted plant and plant parts of the new strawberry variety 'PE-3.222' are between three and four months old. The photographs were taken in Ventura County, Calif.:

DETAILED BOTANICAL DESCRIPTION

Figure 1:
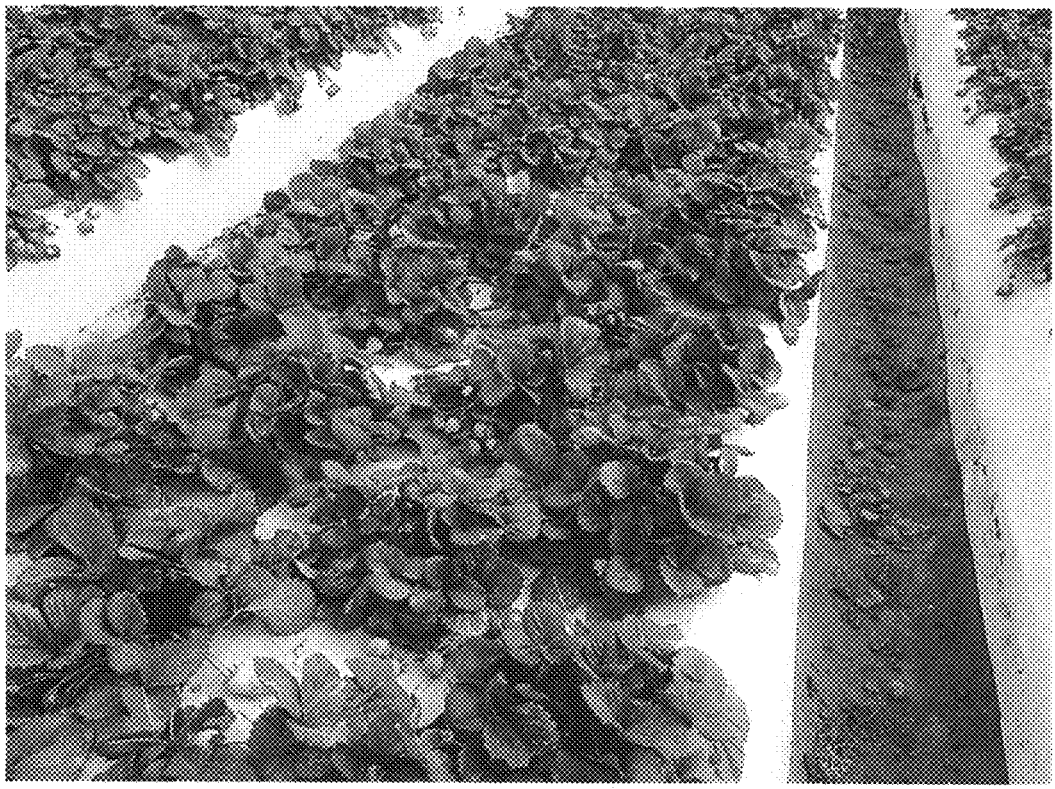
FIG. 1 shows typical fruiting field characteristics of 'PE-3.222', taken in the month of November 2013.
Figure 2:
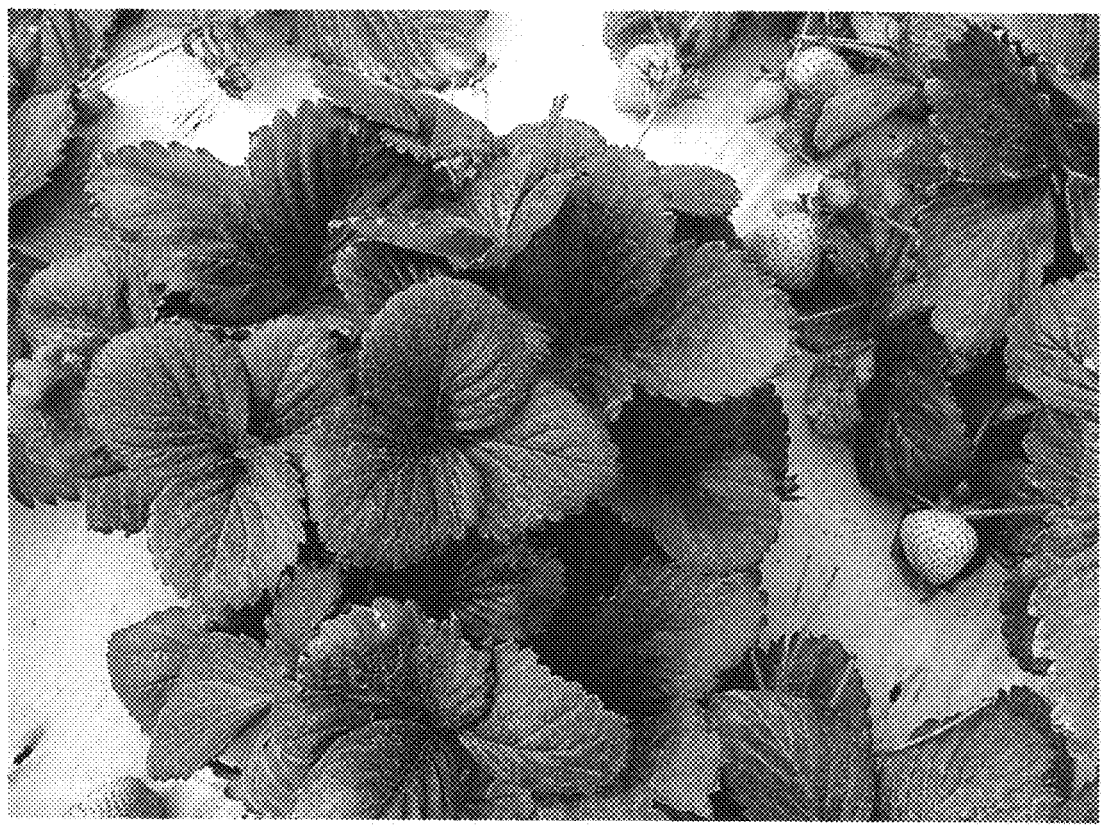
FIG. 2 shows a close-up view of the typical leaf structure of 'PE-3.222', taken in the month of November 2013.
Figure 3:
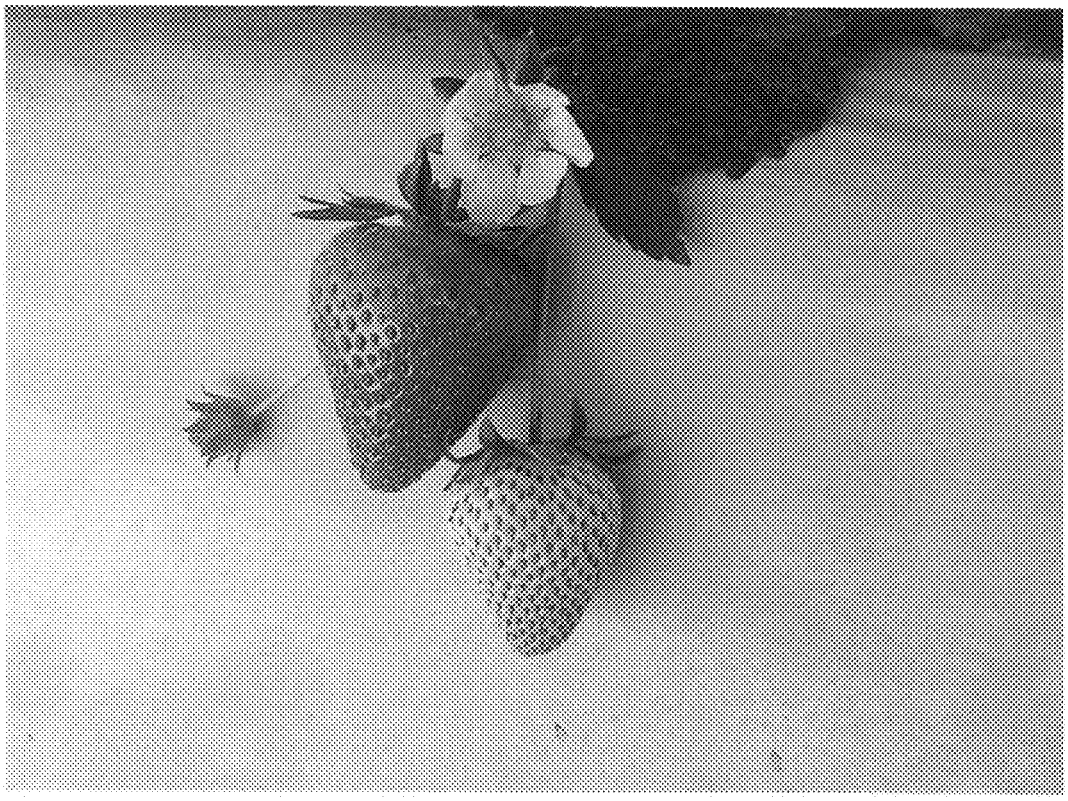
FIG. 3 shows typical mature and immature field fruit of 'PE-3.222', taken in the month of October 2013.
Figure 4:
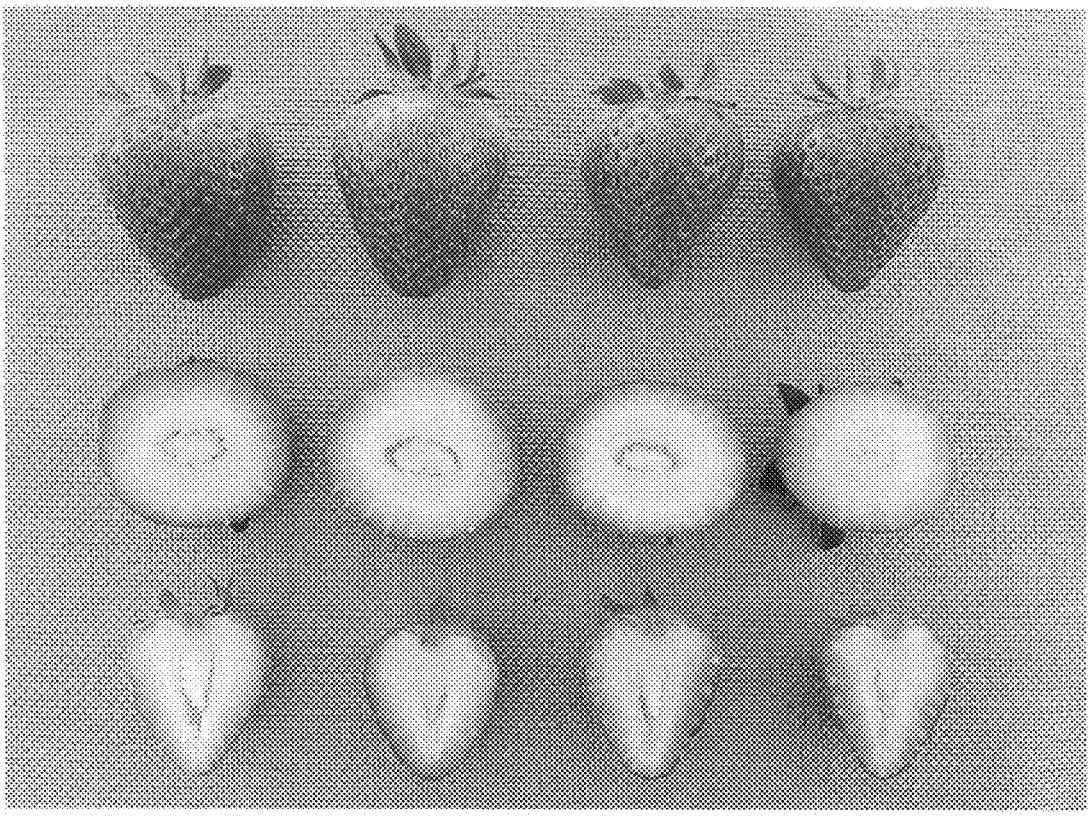
FIG. 4 shows typical internal and external mature fruit characteristics of 'PE-3.222', taken in the month of November 2013.

The new variety 'PE-3.222' has not been observed under all possible environmental conditions. The characteristics of the new variety 'PE-3.222' may vary in detail, depending upon variations in environmental factors, including weather (temperature, humidity and light intensity), day length, soil type and location. In addition, the characteristics of any parental variety or comparison variety included in Tables 1 and 2 of the present invention may vary in detail, depending upon variations in environmental factors, including weather (temperature, humidity and light intensity), day length, soil type and location.

The aforementioned photographs, together with the following description of the new variety 'PE-3.222', unless otherwise noted, are based on observations taken during the 2013 growing season in Ventura County, Calif. These measurements and ratings were taken from plants of 'PE-3.222' dug from a low-elevation nursery located in San Joaquin County, Calif. during January 2013 and planted six months later in Ventura County, Calif. The approximate age of the observed plants is between three and four months. Yield observations including average weight and marketable yield, along with fruit quality characteristics including soluble solids, are averaged from four years of data collected from the 2009 through 2012 growing seasons. Flower measurements and characteristics are from secondary flowers unless otherwise noted. Fruit characteristics and measurements are from secondary fruit unless otherwise noted.

Where noted, color terminology follows The Royal Horticultural Society Colour Chart, London (2007).

The following characteristics describe fruit, plant, stolon, foliage, fruiting truss, flower, and pest and disease characteristics of the new strawberry 'PE-3.222'.

Fruit characteristics:

*Color of mature fruit*.—RHS 34B (ranges from orange to orange red).
*Color of internal flesh*.—RHS 32A (orange red).
*Color of core*.—RHS NN155B (white).
*Length* (*cm*).—4.3.
*Width* (*cm*).—3.7.
*Size*.—Large.
*Length/width ratio*.—1.18 (slightly longer than broad).
*Calyx diameter* (*cm*).—4.2.
*Average weight* (*gm*).—24.5.
*Achene color, shaded side*.—RHS 153D (green group).
*Achene color, sun-exposed side*.—RHS 185A (greyed purple group).
*Achene weight* (*mg*).—0.60.
*Achenes per berry*.—345.
*Marketable yield* (*gm/plant*).—510.
*Predominant shape*.—Conical.
*Difference in shape between primary and secondary fruit*.—Moderate.
*Band without achenes*.—Absent or very narrow.
*Evenness of surface*.—Even or very slightly uneven.
*Evenness of color*.—Slightly uneven.
*Glossiness*.—Ranges from medium to strong.
*Insertion of achenes*.—Level with surface.
*Position of calyx attachment*.—Inserted.
*Attitude of sepals*.—Outward.
*Size of calyx in relation to fruit diameter*.—Slightly larger.
*Adherence of calyx* (*when fully ripe*).—Strong.
*Firmness of flesh*.—Medium.
*Distribution of red color of the flesh*.—Only marginal.
*Hollow center expression*.—Weak.
*Flavor*.—Very good.
*Soluble solids* (*% brix*).—8.3.
*Time of first flowering*.—Ranges from early to medium.
*Time of first harvesting*.—Ranges from early to medium.
*Harvest period*.—Late September to mid December.
*Harvest maturity*.—Early to mid season.
*Type of bearing*.—Fully remontant (non-flowering runners).

Plant characteristics:

*Height* (*cm*).—18.4.
*Spread* (*cm*).—35.0.
*Size*.—Ranges from small to medium.
*Habit*.—Semi-upright.
*Density*.—Medium.
*Vigor*.—Strong.

Stolon characteristics:

*Color*.—RHS 146C (yellow green group).
*Anthocyanin coloration*.—RHS 180B (greyed red group).
*Anthocyanin intensity*.—Ranges from weak to medium.
*Pubescence*.—Dense.
*Attitude of hairs*.—Upward.
*Average quantity* (*nursery*).—Few.
*Average diameter at bract* (*mm*).—3.8 (thick).

Terminal leaflet characteristics:

*Length* (*cm*).—7.4.
*Width* (*cm*).—6.7.
*Length/width ratio*.—1.11 (longer than broad).
*Shape of base*.—Acute.

*Shape of teeth*.—Obtuse (serrate to crenate).
*Serrations per leaf*.—18.8.

Foliage characteristics:
*Color of upper surface*.—RHS 137A (medium green).
*Color of underside*.—RHS 148B (yellow green group).
*Number of leaflets*.—3.
*Size*.—Small.
*Shape in cross section*.—Slightly concave to flat.
*Interveinal blistering*.—Medium.
*Glossiness*.—Medium.
*Variegation*.—Absent.

Petiole characteristics:
*Color*.—RHS 146C (yellow green group).
*Length* (*cm*).—11.8.
*Diameter* (*mm*).—2.6.
*Attitude of hairs*.—Slightly outward.
*Frequency of bract leaflets*.—15% occurrence (few).
*Bract leaflet size*.—Small.
*Pubescence*.—Sparse.
*Petiolule color*.—RHS 146C (yellow green group).
*Petiolule length* (*mm*).—8.6.

Stipule characteristics:
*Color*.—RHS 146C (yellow green group).
*Anthocyanin coloration*.—N/A.
*Anthocyanin intensity*.—Absent or very weak.
*Length* (*mm*).—16.6.
*Width* (*mm*).—9.3.

Fruiting truss characteristics:
*Anthocyanin coloration*.—N/A.
*Anthocyanin intensity*.—Absent or very weak.
*Length at maturity* (*cm*).—19.4.
*Position relative to foliage*.—Beneath.
*Number of flowers*.—Few.
*Pedicel attitude of hairs*.—Strongly outward.
*Pubescence*.—Strong.
*Attitude at first pick*.—Prostrate.

Flower characteristics:
*Petal color*.—RHS NN 155C (white group).
*Sepal color*.—RHS 137A (green group).
*Receptacle color*.—RHS 148B (yellow green group).
*Anther color*.—RHS 15A (yellow group).
*Corolla diameter* (*mm*).—34.0 (ranges from medium to large).
*Calyx diameter* (*mm*).—32.9.
*Petal length* (*mm*).—13.5.
*Petal width* (*mm*).—11.8.
*Petal length/width ratio*.—1.15 (longer than broad).
*Petals/flower*.—5.8.
*Sepal length* (*mm*).—12.2.
*Sepal width* (*mm*).—3.8.
*Sepal length/width ratio*.—3.18.
*Sepals/flower*.—11.8.
*Size of calyx relative to corolla*.—Same.
*Size of inner calyx relative to outer calyx*.—Same.
*Relative position of petals* (*flowers with* 5-6 *petals*).—Touching.
*Stamen*.—Present.

Pest and disease reactions:
*Powdery mildew*.—Moderate.
*Angular leaf spot*.—Moderate.
*Botrytis fruit rot*.—Moderately susceptible.
*Two-spotted spider mite*.—Moderately susceptible.

We claim:

1. A new and distinct strawberry plant named ‘PE-3.222’, as herein described and illustrated by the characteristics set forth above.

* * * * *